United States Patent
Fischer et al.

(10) Patent No.: US 7,368,439 B2
(45) Date of Patent: May 6, 2008

(54) DINUCLEOSIDE POLY(BORANO)PHOSPHATE DERIVATIVES AND USES THEREOF

(75) Inventors: Bilha Fischer, Shoham (IL); Victoria Nahum, Rishon-le-Zion (IL)

(73) Assignee: BAR - ILAN University, Ramat Gan (IL)

(*) Notice: Subject to any disclaimer, the term of this patent is extended or adjusted under 35 U.S.C. 154(b) by 0 days.

(21) Appl. No.: 11/452,244

(22) Filed: Jun. 14, 2006

(65) Prior Publication Data
US 2006/0287271 A1    Dec. 21, 2006

Related U.S. Application Data

(60) Provisional application No. 60/690,472, filed on Jun. 15, 2005, provisional application No. 60/690,475, filed on Jun. 15, 2005.

(51) Int. Cl.
*A61K 31/70* (2006.01)
*C07H 19/10* (2006.01)
*C07H 19/20* (2006.01)

(52) U.S. Cl. .................. 514/47; 514/51; 536/26.22; 536/26.26

(58) Field of Classification Search ............ 514/47, 514/51; 536/26.22, 26.26
See application file for complete search history.

(56) References Cited

U.S. PATENT DOCUMENTS

| | | | |
|---|---|---|---|
| 5,143,907 A * | 9/1992 | Spielvogel et al. ............ 514/64 |
| 5,260,427 A * | 11/1993 | Spielvogel et al. ......... 536/17.1 |
| 5,434,143 A * | 7/1995 | Spielvogel et al. ............ 514/64 |
| 5,763,447 A | 6/1998 | Jacobus et al. |
| 5,789,391 A | 8/1998 | Jacobus et al. |
| 5,837,861 A | 11/1998 | Pendergast et al. |
| 5,900,407 A | 5/1999 | Yerxa et al. |
| 5,968,913 A | 10/1999 | LaCroix et al. |
| 6,022,527 A | 2/2000 | Boucher, Jr. et al. |
| 6,143,279 A | 11/2000 | Boucher, Jr. et al. |
| 6,159,952 A | 12/2000 | Shaffer et al. |
| 6,323,187 B1 | 11/2001 | Yerxa et al. |
| 6,331,529 B1 | 12/2001 | Yerxa et al. |
| 6,348,589 B1 | 2/2002 | Pendergast et al. |
| 6,420,347 B1 | 7/2002 | Jacobus et al. |
| 6,423,694 B1 | 7/2002 | Drutz et al. |
| 6,436,910 B1 | 8/2002 | Yerxa et al. |
| 6,462,028 B2 | 10/2002 | Pendergast et al. |
| 6,555,675 B2 | 4/2003 | Rideout et al. |
| 6,596,725 B2 | 7/2003 | Peterson et al. |
| 6,624,150 B2 | 9/2003 | Yerxa et al. |
| 6,673,779 B2 | 1/2004 | Jacobus et al. |
| 6,696,425 B2 | 2/2004 | Yerxa et al. |
| 6,703,376 B2 | 3/2004 | Jacobus et al. |
| 6,818,629 B2 | 11/2004 | Peterson et al. |
| 6,864,243 B1 | 3/2005 | Peterson |
| 6,867,199 B2 | 3/2005 | Rideout et al. |
| 2005/0065108 A1 | 3/2005 | Fischer et al. |

OTHER PUBLICATIONS

[R] He et al., "Synthesis and Separation of Diastereomers of Ribonucleoside 5'-(alpha-P-Borano)triphosphates," □□Journal of Organic Chemistry, 63(17), 5769-5773 (Jul. 30, 1998).*

Bilha Fischer et al., "2-Thioether 5'-*O*-(1-Thiotriphosphate) adenosine Derivatives as New Insulin Secretagogues Acting through P2Y-Receptors", *J. Med. Chem.*, vol. 42, pp. 3636-3646, 1999.

D. Hillaire-Buys et al., "Stimulation of insulin secretion and improvement of glucose tolerance in rat and dog by the $P_{2y}$-purinoceptor agonist, adenosine-5'*O*-(2-thiodiphosphate)", *Br. J. Pharmacol.*, vol. 109, pp. 183-187, 1993.

G. Ribes et al., "Effects of 2-methylthio ATP on insulin secretion in the dog in vivo", *European Journal of Pharmacology*, vol. 155, pp. 171-174, 1988.

* cited by examiner

*Primary Examiner*—L. E. Crane
(74) *Attorney, Agent, or Firm*—Browdy and Neimark P.L.L.C.

(57) ABSTRACT

The present invention provides dinucleoside boranophosphate derivatives of the general formula I:

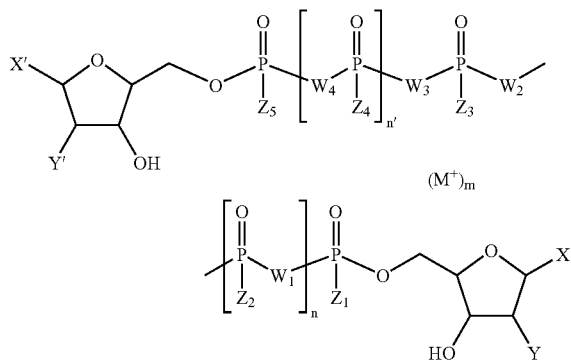

wherein X and X' each independently is an unsubstituted or substituted purine or pyrimidine residue; Y and Y' each independently is H or OH; $Z_1$ to $Z_5$ each independently is O⁻ or $BH_3^-$, but excluding the compounds wherein $Z_1$ to $Z_5$ are each O⁻; $W_1$ to $W_4$ each independently is O, $CH_2$, NH or $C(Halogen)_2$; n and n' each independently is 0 or 1; m is 3, 4 or 5; and M⁺ represents a pharmaceutically acceptable cation, and to pharmaceutical compositions thereof. These dinucleoside boranophosphates are useful for prevention or treatment of diseases or disorders modulated by P2Y receptors such as type 2 diabetes, cystic fibrosis and cancer.

17 Claims, 3 Drawing Sheets

DINUCLEOSIDE POLY(BORANO)PHOSPHATE DERIVATIVES AND USES THEREOF

CROSS-REFERENCE TO RELATED APPLICATIONS

The present application claims the benefit of U.S. Provisional Patent Application Nos. 60/690,472 and 60/690,475, both filed Jun. 15, 2005, now expired, the entire contents of each and all these applications being herewith incorporated by reference in their entirety as if fully disclosed herein.

FIELD OF THE INVENTION

The present invention relates to novel dinucleoside poly(borano)phosphates derivatives and to pharmaceutical compositions comprising them. The compounds are useful for prevention or treatment of diseases or disorders modulated by P2Y-receptors such as diseases associated with a disorder of mucous hydration and type 2 diabetes.

BACKGROUND OF THE INVENTION

Mucociliary Clearance System

Mucous secretions are normally removed via the mucociliary clearance (MCC) system, which relies on the integrated action of mucus secretion by goblet cells and submucosal glands; the movement of cilia on epithelial cells which propels the mucus across the luminal surface; and ion transport into and out of luminal epithelial cells which controls the flow of water into the mucus.

The most common diseases associated with a disorder of mucous hydration, secretion and clearance are diseases of the airways, resulting from retained mucus secretions such as chronic obstructive pulmonary disease, chronic bronchitis, cystic fibrosis, primary ciliary dyskinesia, sinusitis and otitis media, and pneumonia.

Disorders of mucus secretion may also cause improper hydration at other sites of the body, thereby resulting in pathological conditions, such as dry eye disease, nasolacrimal duct obstruction, retinal detachment, glaucoma or ocular hypertension, retinal degeneration, vaginal dryness, gastroesophageal reflux, dry mouth, and constipation.

Enhancement of mucociliary clearance or balanced tissue hydration would thus be useful in the prevention, management and treatment of such disorders. Furthermore, enhancement of mucociliary clearance would also have diagnostic applications such as sputum induction and detection of lung cancer.

P2Y-R Ligands as Potential Drugs for MCC System Disorders

The P2-receptor superfamily, consisting of ligand-gated ion-channels (P2X-Rs) and G-protein coupled receptors (P2Y-Rs), are activated principally by ATP (and by ADP or UTP at several receptor subtypes). P2Y-Rs are attractive pharmaceutical targets due to their involvement in the modulation of many tissues and organs under both normal and pathophysiological conditions, thus making P2Y-R agonist potential drugs. P2Y purinergic receptor agonists are known as modulators of all components of the MCC system. They increase both the rate and total amount of mucin secretion by goblet cells in vitro, increase cilia beat frequency in human airway epithelial cells in vitro, increase Cl$^-$ secretion and, hence, water secretion from airway epithelial cells in vitro, and release surfactant from Type II alveolar cells. In addition to such actions, P2Y agonists also regulate phospholipase C through an extracellular 5'-nucleotide receptor in human airway epithelial cells.

Several U.S. patents disclose dinucleoside polyphosphates said to be highly selective P2Y purinergic receptors agonists and useful in the prevention, management or treatment of diseases and disorders associated with abnormalities of tissue fluid secretion, hydration and clearance, including chronic obstructive pulmonary diseases (chronic bronchitis, primary ciliary dyskinesia, cystic fibrosis, immobility-associated pneumonia), sinusitis, otitis media, nasolacrimal duct obstruction, dry eye disease, glaucoma, retinal degeneration and edematous retinal disorders including retinal detachment, vaginal dryness, and gastrointestinal tract disease (e.g. U.S. Pat. Nos. 6,555,675, 6,867,199, 5,837,861, 6,348,589, 6,420,347, 6,673,779, 5,789,391, 5,763,447, 6,703,376, 5,968,913, 6,331,529, 6,436,910, 6,323,187, 6,143,279, 6,022,527, 6,159,952, 6,423,694, 6,596,725, 6,818,629, 5,900,407, 6,696,425, 6,864,243, 6,624,150 and 6,462,028).

Pathophysiology of Diabetes Mellitus

Diabetes mellitus is one of the most prevalent chronic diseases in the Western world, affecting up to 5% of the population. It is a heterogenous group of disorders characterized by a chronic hyperglycemia—results from defects in insulin secretion, insulin action, or a combination of both—with additional abnormalities in lipid and protein metabolism. In addition to its chronic metabolic abnormalities, diabetes is associated with long-term complications involving various organs, especially the eyes, nerves, blood vessels, heart and kidney, which may result in blindness, amputations, cardiovascular disease and end stage renal disease. The development of diabetic complications appears to be related to the chronic elevation of blood glucose. There is no current cure for diabetes, however, effective glycemic control can lower the incidence of diabetic complications and reduce their severity.

The two major forms of diabetes are classified as type 1 and type 2, previously termed non-insulin-dependent diabetes mellitus (NIDDM), which affect approximately 95% of patients with diabetes.

Type 2 diabetes appears to be a complex polygenic disease in which insulin resistance and relative insulin deficiency coexist. Thus, improvement of insulin secretion is a major therapeutic goal. The deficiency of insulin release expresses itself not only by the absence of first-phase insulin response to glucose, but also by a global reduction in the magnitude of insulin release to 10-20% of the normal secretory capacity (Cerasi, 1992). Patients with type 2 diabetes are treated with various oral antidiabetic agents, insulin injections, or a combination of both. The currently available oral antidiabetic drugs are targeted at either reducing peripheral insulin resistance, increasing insulin secretion from the pancreatic beta-cell, or slowing the absorption of carbohydrates from the intestine.

Approximately half of the patients with type 2 diabetes are treated with oral agents, a considerable proportion of them with agents that stimulate insulin secretion. The choice of insulin secretagogues is limited to the sulfonylureas and related compounds ("glinides"), which elicit insulin secretion by binding to a regulatory subunit of membrane ATP-sensitive potassium channel, inducing its closure (Lebovitz, 1994). Nevertheless, sulfonylureas have several undesired effects in addition to possible long-term adverse effect on their specific target, the pancreatic beta-cell. These side-effects include the risk of hypoglycemia due to stimulation of insulin secretion at low glucose concentrations, the difficulty of achieving normal glycemia in a significant number of patients, the annually 5-10% secondary failure rate of adequate glycemic control, and possible negative effects on the cardiovascular system (Lebovitz, 1994; Leibowitz and Cerasi, 1996; Brady and Terzic, 1998). Two types of agents are used to attenuate peripheral insulin resistance: the biguanide metformin and the thiazolidinedione analogues (Edelman, 1998). The α-glucosidase inhibitor, pseudotetrasaccharide acarbose, is used to slow intestinal absorption of carbohydrates.

P2Y-R Ligands as Potential Antidiabetic Drugs

The presence of P2Y-Rs on pancreatic beta cells is well documented (Loubatières-Mariani et al., 1979; Chapal and Loubatières-Mariani, 1981; Bertrand et al., 1987; Bertrand et al., 1991) and their activation results in stimulation of insulin secretion at stimulating glucose concentrations. The mechanism whereby P2Y-R agonists enhance glucose-induced insulin release may involve the cyclic AMP/Protein Kinase A signaling pathway (Petit et al., 2000), which has been reported to increase the effectiveness of the $K^+_{ATP}$ channel-independent action of glucose (Yajima et al., 1999).

Various P2-R selective ligands have been shown to increase insulin secretion and decrease glycemia in vivo (Ribes et al., 1988; Hillaire-Buys et al., 1993). The list of ligands include 2-methylthio-ATP, which breaks down rapidly into adenosine thus was injected directly to the pancreatico-duodenal artery (Ribes et al., 1988), and adenosine 5'-O-(2-thio)diphosphate, which is stable to enzymatic hydrolysis thus was administered either intravenously or orally (Hillaire-Buys et al., 1993).

Almost all current synthetic P2-receptor agonists are modifications of the ATP or UTP pharmacophore. The purine (pyrimidine) ring system, the ribose moiety, or the triphosphate chain are modified at one or more positions (Fischer, 1999). Previously, we have reported the synthesis of ATP derivatives bearing a long thioether substitution at C-2 position, such as 2-thioether-5'-O-(1-thiotriphosphate) adenosine derivatives (Fischer et al., 1999). WO 03/034978 of the same applicant discloses 2-substituted-5'-O-(1-boranotriphosphate)-adenosine derivatives that act through P2Y (ATP/UTP)-receptors, present in the membrane of pancreatic beta cells, as insulin secretagogues with high efficacy and potency, enhancing insulin secretion at the nM concentration range, under slightly stimulatory glucose concentration.

SUMMARY OF THE INVENTION

The present invention relates to dinucleoside poly(borano)phosphate derivatives in which at least one oxygen atom of one phosphate moiety is replaced by a borano ($BH_3$) radical.

In one aspect, the present invention relates to a dinucleoside poly(borano)phosphate derivative of the general formula I:

wherein

X and X' each independently is a purine residue of the formula Ia:

wherein

$R_1$ is selected from the group consisting of H, halogen, O-hydrocarbyl, S-hydrocarbyl, $NR_4R_5$, heteroaryl, unsubstituted hydrocarbyl and hydrocarbyl substituted by halogen, CN, SCN, $NO_2$, $OR_4$, $SR_4$, $NR_4R_5$ or heteroaryl, wherein $R_4$ and $R_5$ each independently is H or hydrocarbyl or $R_4$ and $R_5$ together with the nitrogen atom to which they are attached form a saturated or unsaturated heterocyclic ring optionally containing 1-2 further heteroatoms selected from the group consisting of oxygen, nitrogen and sulfur, the additional nitrogen being unsubstituted or substituted by alkyl substituted by halogen, hydroxyl or phenyl;

$R_2$ is H or absent;

$R_3$ is O or $NHR_6$ wherein $R_6$ is H or hydrocarbyl; and the dotted line represents a potential double bond between the carbon atom at position 6 and either the nitrogen atom at position 1 or the radical $R_3$, provided that, when $R_2$ is H, there is a double bond between the carbon atom at position 6 and $R_3$, and when $R_2$ is absent, there is a double bond between the carbon atom at position 6 and the nitrogen atom at position 1, and the purine residue is linked through the N-9 bond to the 1' carbon of the pentose;

or X and X' each independently is a pyrimidine residue of the formula Ib:

wherein $R_7$ and $R_8$ each independently is H, halogen, O-hydrocarbyl, S-hydrocarbyl, $NR_{11}R_{12}$, heteroaryl, unsubstituted hydrocarbyl or hydrocarbyl substituted by halogen, CN, SCN, $NO_2$, $OR_{11}$, $SR_{11}$, $NR_{11}R_{12}$ or heteroaryl, wherein $R_{11}$ and $R_{12}$ each independently is H or hydrocarbyl, or $R_{11}$ and $R_{12}$ together with the nitrogen atom to which they are attached form a saturated or unsaturated heterocyclic ring optionally containing 1-2 further heteroatoms selected from the group consisting of oxygen, sulfur and nitrogen, the additional nitrogen being unsubstituted or substituted by alkyl substituted by halogen, hydroxyl or phenyl;

$R_9$ is O or $NHR_{13}$ wherein $R_{13}$ is H or hydrocarbyl;

$R_{10}$ is H or absent; and the dotted line represents a potential double bond between the carbon atom at position 4 and either the nitrogen atom at position 3 or the radical $R_9$, provided that, when $R_{10}$ is H, there is a double bond between the carbon atom at position 4 and $R_9$, and when $R_{10}$ is absent, there is a double bond between the carbon atom at position 4 and the nitrogen atom at position 3, and the pyrimidine residue is linked through the N-1 bond to the 1' carbon of the pentose;

Y and Y' each independently is H or OH;

$Z_1$, $Z_2$, $Z_3$, $Z_4$ and $Z_5$ each independently is $O^-$ or $BH_3^-$, but at least one is $BH_3^-$;

$W_1$, $W_2$, $W_3$ and $W_4$ each independently is O, $CH_2$, NH or $C(Hal)_2$, wherein Hal is halogen, preferably F or Cl;

n and n' each independently is 0 or 1;

m is 3, 4 or 5; and $M^+$ represents a pharmaceutically acceptable cation, and diastereoisomers thereof.

In another aspect, the present invention relates to a pharmaceutical composition for prevention or treatment of a disease or disorder modulated by P2-Y receptors, comprising at least one dinucleoside poly(borano)phosphate derivative of the general formula I and a pharmaceutically acceptable carrier or diluent.

In a further aspect, the present invention relates to a method of preventing, managing or treating a disease or disorder modulated by P2-Y receptors, which comprises administering to an individual in need an effective amount of a compound of the general formula I.

BRIEF DESCRIPTION OF THE FIGURES

FIG. 3 shows the insulin secretion level in human islets induced by various concentrations of diuridine poly(borano)phosphate $Up_3(\beta$-B)U tri-sodium salt. Islets aliquots were supplemented with 1 ml of medium containing 2.2, 12 or 22 mM glucose, or 22 mM glucose with 3-isobutyl-1-methylxanthine (IBMX) as a positive control, in the presence of various concentration of $Up_3(\beta$-B)U tri-sodium salt, and incubated for 30 minutes at 37° C. in a humidified atmosphere containing 5% $CO_2$. The medium was then collected for determination of insulin level; islets were collected for determination of protein; and insulin secretion was normalized to total protein. Basal insulin secretion was determined by incubating the islets in the presence of buffer containing 2 mM glucose. As shown, under conditions of 12 mM glucose, $Up_3(\beta$-B)U tri-sodium salt at $10^{-13}$ and $10^{-12}$ M was able to promote significant insulin secretion by human islets.

DETAILED DESCRIPTION OF THE INVENTION

The present invention relates, in one aspect, to a dinucleoside poly(borano)phosphate derivative of the general formula I herein.

In the compounds of formula I, X and X' may both be the same or different purine or pyrimidine residue, or one of X and X' is a purine residue and the other is a pyrimidine residue.

As used herein in the compounds of formula I, the term "halogen" includes fluoro, chloro, bromo, and iodo, and is preferably chloro or bromo.

The term "hydrocarbyl" in any of the definitions of the different radicals $R_1$ to $R_{13}$ refers to a radical containing only carbon and hydrogen atoms that may be saturated or unsaturated, linear or branched, cyclic or acyclic, or aromatic, and includes $C_1$-$C_8$ alkyl, $C_2$-$C_8$ alkenyl, $C_2$-$C_8$ alkynyl, $C_3$-$C_{10}$ cycloalkyl, $C_3$-$C_{10}$ cycloalkenyl, $C_6$-$C_{14}$ aryl, $(C_1$-$C_8)$alkyl$(C_6$-$C_{14})$aryl, and $(C_6$-$C_{14})$ aryl$(C_1$-$C_8)$alkyl.

The term "$C_1$-$C_8$ alkyl" typically means a straight or branched hydrocarbon radical having 1-8 carbon atoms and includes, for example, methyl, ethyl, n-propyl, isopropyl, n-butyl, sec-butyl, isobutyl, tert-butyl, n-pentyl, 2,2-dimethylpropyl, n-hexyl, n-heptyl, n-octyl, and the like. Preferred are $C_1$-$C_6$ alkyl groups, most preferably methyl. The terms "$C_2$-$C_8$ alkenyl" and "$C_2$-$C_8$ alkynyl" typically mean straight and branched hydrocarbon radicals having 2-8 carbon atoms and 1 double or triple bond, respectively, and include ethenyl, 3-buten-1-yl, 2-ethenylbutyl, 3-octen-1-yl, and the like, and propynyl, 2-butyn-1-yl, 3-pentyn-1-yl, and the like. $C_2$-$C_6$ alkenyl radicals are preferred. The term "$C_3$-$C_{10}$ cycloalkyl" means a cyclic or bicyclic hydrocarbyl group such as cyclopropyl, cyclobutyl, cyclopentyl, cyclohexyl, adamantyl, bicyclo[3.2.1]octyl, bicyclo[2.2.1]heptyl, and the like. The term "$C_6$-$C_{14}$ aryl" denotes a carbocyclic aromatic radical such as phenyl and naphthyl and the term "ar($C_1$-$C_8$)alkyl" denotes an arylalkyl radical such as benzyl and phenetyl.

When the radical $R_1$ is a O-hydrocarbyl or S-hydrocarbyl radical or is hydrocarbyl substituted by a $OR_4$ or $SR_4$ radical, wherein $R_4$ is hydrocarbyl, $R_4$ is preferably a $C_1$-$C_6$ alkyl, most preferably methyl, or an aryl, most preferably phenyl, or an aralkyl, most preferably benzyl, radical.

When the radical $R_3$ is a hydrocarbyl, $R_3$ is preferably a $C_1$-$C_6$ alkyl, most preferably methyl, or an aryl, most preferably phenyl, or an aralkyl, most preferably benzyl, radical.

When the radical $R_7$ or $R_8$ is a O-hydrocarbyl or S-hydrocarbyl radical or is hydrocarbyl substituted by a $OR_{11}$ or $SR_{11}$ radical, wherein $R_{11}$ is hydrocarbyl, $R_{11}$ is preferably a $C_1$-$C_6$ alkyl, most preferably methyl, or an aryl, most preferably phenyl, or an aralkyl, most preferably benzyl, radical.

When the radical $R_{13}$ is a hydrocarbyl, $R_{13}$ is preferably a $C_1$-$C_6$ alkyl, most preferably methyl, or an aryl, most preferably phenyl, or an aralkyl, most preferably benzyl, radical.

In the group $NR_4R_5$, $R_4$ and $R_5$ each independently is H or hydrocarbyl as defined above or form together with the N atom to which they are attached a saturated or unsaturated, preferably a 5- or 6-membered, heterocyclic ring, optionally containing 1 or 2 further heteroatoms selected from nitrogen, oxygen, and sulfur. Such rings may be substituted, for example with one or two $C_1$-$C_6$ alkyl groups, or with one alkyl or hydroxyalkyl group at a second nitrogen atom of the ring, for example in a piperazine ring. Examples of radicals $NR_4R_5$ include, without being limited to, amino, dimethylamino, diethylamino, ethylmethylamino, phenylmethylamino, pyrrolidino, piperidino, tetrahydropyridino, piperazino, ethylpiperazino, hydroxyethylpiperazino, morpholino, thiomorpholino, thiazolino, and the like.

In the group $NHR_6$, $R_6$ is H or hydrocarbyl as defined above or form together with the N atom to which they are attached a saturated or unsaturated, preferably a 5- or 6-membered, heterocyclic ring, optionally containing 1 or 2 further heteroatoms selected from nitrogen, oxygen, and sulfur. Such rings may be substituted, for example with one or two $C_1$-$C_6$ alkyl groups, or with one alkyl or hydroxyalkyl group at a second nitrogen atom of the ring, for example in a piperazine ring.

In the group $NR_{11}R_{12}$, $R_{11}$ and $R_{12}$ each independently is H or hydrocarbyl as defined above or form together with the N atom to which they are attached a saturated or unsaturated, preferably a 5- or 6-membered, heterocyclic ring, optionally containing 1 or 2 further heteroatoms selected from nitrogen, oxygen, and sulfur. Such rings may be substituted, for example with one or two $C_1$-$C_6$ alkyl groups, or with one alkyl or hydroxyalkyl group at a second nitrogen atom of the ring, for example in a piperazine ring. Examples of radicals $NR_{11}R_{12}$ include, without being limited to, amino, dimethylamino, diethylamino, ethylmethylamino, phenylmethylamino, pyrrolidino, piperidino, tetrahydropyridino, piperazino, ethylpiperazino, hydroxyethylpiperazino, morpholino, thiomorpholino, thiazolino, and the like.

In the group $NHR_{13}$, $R_{13}$ is H or hydrocarbyl as defined above or form together with the N atom to which they are attached a saturated or unsaturated, preferably a 5- or 6-membered, heterocyclic ring, optionally containing 1 or 2 further heteroatoms selected from nitrogen, oxygen, and sulfur. Such rings may be substituted, for example with one or two $C_1$-$C_6$ alkyl groups, or with one alkyl or hydroxyalkyl group at a second nitrogen atom of the ring, for example in a piperazine ring.

The term "heteroaryl" refers to a radical derived from a mono- or poly-cyclic ring containing one to three heteroatoms selected from the group consisting of N, O and S, with unsaturation of aromatic character. Non-limiting examples of heteroaryl include pyrrolyl, furyl, thienyl, pyrazolyl, imidazolyl, oxazolyl, isoxazolyl thiazolyl, isothiazolyl, pyridyl, 1,3-benzodioxinyl, pyrazinyl, pyrimidinyl, 1,3,4-triazinyl, 1,2,3-triazinyl, 1,3,5-triazinyl, thiazinyl, quinolinyl, isoquinolinyl, benzofuryl, isobenzofuryl, indolyl, imidazo[1,2-a]pyridyl, pyrido[1,2-a]pyrimidinyl, benzimidazolyl, benzthiazolyl, benzoxazolyl. The heteroaryl ring may be substituted. It is to be understood that when a polycyclic heteroaromatic ring is substituted, the substitution may be in the heteroring or in the carbocyclic ring.

In one embodiment, the compound of formula I has two purine, preferably, adenosine, residues, and has the formula:

In another embodiment, the compound of formula I has two pyrimidine, preferably, uridine, residues, and has the formula:

In another embodiment, the compound of formula I has a purine and a pyrimidine residue.

In one embodiment, the dinucleoside poly(borano)phosphate derivative is a penta(borano)phosphate, that may contain 1-5 $BH_3^-$ groups. In another embodiment, the dinucleoside poly(borano)phosphate derivative is a tetra(borano) phosphate, that may contain 1-4 $BH_3^-$ groups. In a further embodiment, the dinucleoside poly(borano)phosphate derivative is a tri(borano)phosphate, that may contain 1-3 $BH_3^-$ groups. Preferred compounds are those containing 1 or 2 $BH_3^-$ groups.

In one embodiment of the present invention, the compound of formula I is a dinucleoside penta(borano)phosphate wherein n and n' are 1, $W_1$ to $W_4$ are O, and 1 to 5 of $Z_1$ to $Z_5$ are $BH_3^-$. This derivative may have a sole borano group at position α (or α'), namely, $Z_1$ (or $Z_5$) is $BH_3^-$ and $Z_2$, $Z_3$, $Z_4$ and $Z_5$ (or $Z_1$) are $O^-$; at position β (or β'), namely, $Z_2$ (or $Z_4$) is $BH_3^-$ and $Z_1$, $Z_3$, $Z_5$ and $Z_4$ (or $Z_2$) are $O^-$; or at position γ, namely, $Z_3$ is $BH_3^-$ and $Z_1$, $Z_2$, $Z_4$ and $Z_5$ are $O^-$.

In another embodiment, the compound of formula I is a dinucleoside penta(borano)phosphate wherein n and n' are 1, $W_1$ to $W_4$ are O, and it has two borano groups at positions α,β (or α',β'), namely, $Z_1$ and $Z_2$ (or $Z_4$ and $Z_5$) are $BH_3^-$ and $Z_3$, $Z_4$ and $Z_5$ (or $Z_1$, $Z_2$ and $Z_3$) are $O^-$; at positions β,γ (or β',γ), namely, $Z_2$ and $Z_3$ (or $Z_3$ and $Z_4$) are $BH_3^-$ and $Z_1$, $Z_4$ and $Z_5$ (or Z1, $Z_2$ and $Z_5$) are $O^-$; at positions α,γ (or α',γ), namely, $Z_1$ (or $Z_5$) and $Z_3$ are $BH_3^-$ and $Z_2$, $Z_4$ and $Z_5$ (or $Z_1$) are $O^-$; at positions α,β' (or α',β), namely, $Z_1$ and $Z_4$ (or $Z_2$ and $Z_5$) are $BH_3^-$ and $Z_2$, $Z_3$ and $Z_5$ (or $Z_1$, $Z_3$ and $Z_4$) are $O^-$; at positions α,α' ($Z_1$, $Z_5$); or at positions β,β' ($Z_2$, $Z_4$).

In a further embodiment, the compound of formula I is a dinucleoside penta(borano)phosphate wherein n and n' are 1, $W_1$ to $W_4$ are O, and it has three borano groups at positions α,β,γ (or α',β',γ), namely, $Z_1$, $Z_2$, and $Z_3$ (or $Z_5$, $Z_4$ and $Z_3$) are $BH_3^-$ and $Z_4$ and $Z_5$ (or $Z_1$ and $Z_2$) are $O^-$; at positions α,β,α' ($Z_1$, $Z_2$, $Z_5$); at positions α,β,β' ($Z_1$, $Z_2$, $Z_4$); at positions α',β,β' ($Z_2$, $Z_4$, $Z_5$); at positions α,α',β' ($Z_1$, $Z_4$, $Z_5$); at positions α',β,γ ($Z_2$, $Z_3$, $Z_5$); at positions α,β',γ ($Z_1$, $Z_3$, $Z_4$); or at positions β,γ,β' ($Z_2$, $Z_3$, $Z_4$).

In another embodiment of the present invention, the compound of formula I is a dinucleoside tetra(borano) phosphate wherein n is 0 and n' is 1, $W_2$ to $W_4$ are O, and 1 to 4 of $Z_1$ and $Z_3$ to $Z_5$ are $BH_3^-$. This derivative may have a sole borano group at position α (or α'), namely, $Z_1$ (or $Z_5$) is $BH_3^-$ and $Z_3$, $Z_4$ and $Z_5$ (or $Z_1$) are $O^-$; or at position β (or β'), namely, $Z_3$ (or $Z_4$) is $BH_3^-$, and $Z_1$, $Z_4$ (or $Z_3$) and $Z_5$ are $O^-$.

In another embodiment, the compound of formula I is a dinucleoside tetra(borano)phosphate wherein n is 0 and n' is 1, $W_2$ to $W_4$ are O, and it has two borano groups at positions α,β (or α',β'), namely, $Z_1$ and $Z_3$ (or $Z_4$ and $Z_5$) are $BH_3^-$ and $Z_4$ and $Z_5$ (or $Z_1$ and $Z_3$) are $O^-$; at positions β,β', namely, $Z_3$ and $Z_4$ are $BH_3^-$ and $Z_1$ and $Z_5$ are $O^-$; at positions α,α' ($Z_1$, $Z_5$); at positions α,β' ($Z_1$, $Z_4$); or at positions (α',β).

In a further embodiment, the compound of formula I is a dinucleoside tetra(borano) phosphate wherein n is 0 and n' is 1, $W_2$ to $W_4$ are O, and it has three borano groups at positions α,β,β' (or α',β,β'), namely, $Z_1$, $Z_3$ and $Z_4$ (or $Z_5$, $Z_4$ and $Z_3$) are $BH_3^-$ and $Z_5$ (or $Z_1$) is $O^-$; at positions α,α',β ($Z_1$, $Z_3$, $Z_5$); or at positions α,α',β' ($Z_1$, $Z_4$, $Z_5$).

In another embodiment of the present invention, the compound of formula I is a dinucleoside tri(borano)phosphate wherein n and n' are 0, $W_2$ and $W_3$ are O, and 1 to 3 of $Z_1$, $Z_3$ and $Z_5$ are $BH_3^-$. This derivative may have a sole borano group at position α (or α'), namely, $Z_1$ (or $Z_5$) is $BH_3^-$ and $Z_3$ and $Z_5$ (or $Z_1$) are $O^-$; or at position β, namely, $Z_3$ is $BH_3^-$ and $Z_1$ and $Z_5$ are $O^-$.

In another embodiment, the compound of formula I is a dinucleoside tri(borano)phosphate wherein n and n' are 0, $W_2$ and $W_3$ are O, and it has two borano groups at positions α,β (or α',β), namely, $Z_1$ (or $Z_5$) and $Z_3$ are $BH_3^-$ and $Z_5$ (or $Z_1$) is $O^-$; or at positions α,α' ($Z_1$, $Z_5$).

In a further embodiment, the compound of formula I is a dinucleoside tri(borano)phosphate wherein n and n' are 0, $W_2$ and $W_3$ each is O, and it has three borano groups at positions α,β,α', namely, $Z_1$, $Z_3$ and $Z_5$ are $BH_3^-$.

Preferred compounds according to the present invention are those wherein X and X' are a purine residue, wherein $R_1$ is H, $R_2$ is absent, and $R_3$ is $NH_2$; Y and Y' are OH; $Z_1$, $Z_2$, $Z_4$ and $Z_5$ are $O^-$; $Z_3$ is $BH_3^-$; $W_1$, $W_2$, $W_3$ and $W_4$ are O; and either n and n' are 0 and m is 3, or n and n' are 1 and m is 5; and those wherein X and X' are a pyrimidine residue, wherein $R_7$, $R_8$ and $R_{10}$ are H, and $R_9$ is O; Y and Y' are OH; $Z_1$, $Z_2$, $Z_4$ and $Z_5$ are $O^-$; $Z_3$ is $BH_3^-$; $W_1$, $W_2$, $W_3$ and $W_4$ are O; and either n and n' are 0 and m is 3, or n and n' are 1 and m is 5.

In one preferred embodiment, the compound of general formula I is diadenosine tri(borano)phosphate salt, the compound of formula I wherein X and X' are adenosine; Y and Y' are OH; $R_1$ is H; $R_2$ is absent; $R_3$ is $NH_2$; $Z_1$ and $Z_5$ each is $O^-$; $Z_3$ is $BH_3^-$; $W_2$ and $W_3$ each is O; n and n' each is 0; m is 3; herein identified as compound 1 or $Ap_3$(β-B)A, and characterized herein in the form of its tributylammonium salt ($M^+$ is tributylammonium).

In another preferred embodiment, the compound of general formula I is diadenosine penta(borano)phosphate salt, wherein X and X' are adenosine; Y and Y' are OH; $R_1$ is H; $R_2$ is absent; $R_3$ is $NH_2$; $Z_1$, $Z_2$, $Z_4$ and $Z_5$ each is $O^-$; $Z_3$ is $BH_3^-$; $W_1$, $W_2$ $W_3$ and $W_4$ each is O; n and n' each is 1; m is 5; herein identified as compound 3 or $Ap_5$(γ-B)A, and characterized herein in the form of its tributylammonium salt ($M^+$ is tributylammonium).

In a further preferred embodiment, the compound of general formula I is diuridine tri(borano)phosphate, wherein X and X' are a pyrimidine residue, wherein $R_7$ and $R_8$ are each H; $R_9$ is O and $R_8$ is H; Y and Y' are each OH; $Z_1$ and $Z_5$ each is $O^-$; $Z_3$ is $BH_3^-$; $W_2$ and $W_3$ each is O; n and n' each is 0; m is 3; herein identified as compound 2 or $Up_3$(β-B)U, and characterized herein in the form of its tributyl-ammonium salt ($M^+$ is tributylammonium).

In yet a further preferred embodiment, the compound of general formula I is diuridine penta(borano)phosphate, wherein X and X' are a pyrimidine residue, wherein $R_7$ and $R_8$ are each H; $R_9$ is O and $R_8$ is H; Y and Y' each is OH; $Z_1$, $Z_2$, $Z_4$ and $Z_5$ each is $O^-$; $Z_3$ is $BH_3^-$; $W_1$, $W_2$ $W_3$ and $W_4$ each is O; n and n' each is 1; m is 5; herein identified as compound 4 or $Up_5$(γ-B)U, and characterized herein in the form of its tributylammonium salt ($M^+$ is tributylammonium).

The invention encompasses the compounds of formula I, the diastereoisomers thereof as well as pharmaceutically acceptable salts thereof such as, but not limited to, compounds wherein $M^+$ is $Na^+$, $K^+$, $NH_4^+$ or the cation of an amine, particularly of a tertiary amine, e.g. $N(R)_3H^+$, wherein R is preferably $C_1$-$C_6$ alkyl, such as methyl, ethyl, propyl, isopropyl, butyl, and the like.

Several chemical methods have been developed to form the pyrophosphate bond in dinucleoside polyphosphates. Dinucleoside polyphosphates are conventionally prepared via the activation of 5'-terminal phosphate of nucleotide thus forming phosphoryl donor (P-donor) followed by reaction with non-activated nucleotides (phosphoryl acceptor, P-acceptor). Nucleotides activated with 5'-phosphoroimidazolide (Hoard and Ott, 1965), 5'-phosphomorpholidates (Moffat, 1964) or phosphoropiperididate (Kadokura et al., 1997) are used as phosphoryl donors for the synthesis. Phosphoroimidazolide was found to be the most reactive donor in the presence of divalent metal ions such as $Mg^{2+}$, $Zn^{2+}$, and $Mn^{2+}$. $Zn^{2+}$ was found to be the best catalyst for a pyrophosphate bond formation between GDP and methyl phosphoroimidazolide in anhydrous DMF (Kadokura et al, 1997). Formation of pyrophosphate bond was achieved also from adenosine 5'-phosphorimidazolide and ADP in aqueous solution using $Mn^{2+}$ and $Cd^{2+}$ metal ion catalysts (Shimazu et al., 1990).

Phosphorimidazolides may be generated in-situ by 1,1'-carbonyldimidazole (CDI) or isolated prior to the reaction with the corresponding nucleotides (Zatorski, 1995). Additional nucleotide coupling procedures include the use of N,N'-dicyclohexylcarbodiimide (DCC) (Chambers et al., 1957) or 1-ethyl-3-(3-dimethylaminopropyl)-carbodiimide (EDC) (Garrison et al., 1993) for the synthesis of dinucleoside polyphosphates. By these procedures, dinucleoside polyphosphates with phosphate linker ranging from 2-6 phosphates have been synthesized (Goldman et al., 1960; Shimazu et al., 1990).

The synthesis of the novel compounds of the invention, herein designated 1-4, required a novel building block, inorganic boranophosphate, BPi, 5, as a phosphoryl acceptor.

Recently, we reported the preparation of boranophosphate salts, 5, and the exploration of their properties (Nahum and Fischer, 2004; International Application No. PCT/IL2005/000118). BPi salts were easily prepared in excellent yield in a one-pot two-step reaction comprising reacting tris(trimethylsilyl)-phosphite with borane-dimethylsulfide complex of the formula $BH_3.SMe_2$, and reacting the intermediate with the desired base ($Bu_3N$) in water or in methanol, thus obtaining the corresponding salt BPi ($Bu_3NH^+$)$_2$ in very high yield (see Scheme 1 hereinafter). BPi salts were characterized by X-ray crystal structure, IR, and $^1H$ and $^{31}P$ NMR.

Substitution of the phosphate, Pi, oxygen by $BH_3$ group results in a significant change of the chemical nature of BPi as compared to Pi. Specifically, the reducing nature of the $BH_3$ moiety is drastically decreased in BPi. Likewise, the nucleophilicity of BPi's oxygen diminishes as compared to Pi, possibly due to the extensive H-bonded clustering in organic solvents (Nahum and Fischer, 2004). Based on its water solubility, acid-base character, H-bonding properties and high stability, BPi appears as a perfect mimic of Pi and is an attractive alternative to the known phosphate isosters.

For the synthesis of $Np_3(B)N$ 1-2 and $Np_5(B)N$ 3-4 compounds 5'-mono- or di-nucleotides activated as the corresponding phosphoroimidazolide were considered as P-donors. Yet, due to the low nucleophilicity of BPi, its application as a P-acceptor (a nucleophile) requires pre-activation. For this purpose, we added $Mg^{2+}$ ions to the reaction mixture. These ions coordinate with BPi and break the extensive H-bonded clustering of BPi in organic solvents, which reduces BPi's nucleophilicity.

Briefly, the synthesis of the novel dinucleoside poly(borano)phosphate analogues 1-4 involves the activation of the nucleotide (e.g. AMP or UMP) tributylammonium salt with 1,1'-carbonyldiimidazole (CDI) in dry DMF at room temperature for 2.5 h, followed by the addition of BPi and $MgCl_2$, and stirring at room temperature for about 20 h. Analogues 1-4 were formed as the exclusive product in good to high yields. Yet, formation of $Np_5(B)N$, 3-4, product was less efficient than that of $Np_3(B)N$, 1-2 analogues. No analogue 1-4 is formed if BPi is pre-activated by CDI, namely, plays the role of a P-donor.

In this reaction, three reactant molecules (two P-donors and one P-acceptor) react concertedly. Yet, even at a 4-fold reaction dilution, or with the addition of a higher number of BPi equivalents (4 eq), $Np_n(B)N$ analogues were still the sole products formed. No $Np_n(B)$ analogues resulting from the reaction of one P-donor and one P-acceptor were formed under these conditions.

Various divalent metal-ions, such as $Zn^{2+}$, $Cd^{2+}$, $Mn^{2+}$, and $Mg^{2+}$, are reported to facilitate nucleotide and dinucleoside polyphosphate synthesis from the corresponding P-acceptor and P-donor (Sawai et al., 1992). However, here, the reaction to produce $Np_n(B)N$ is metal-ion specific. The metal-ion activator is limited only to $Mg^{2+}$ ions. Specifically, the synthesis of $Np_n(B)N$ analogues was attempted with various other metal-ions. Replacing $Mg^{2+}$ by $Ca^{2+}$, $Ni^{2+}$, and $Cu^{2+}$ produced no $Np_n(B)N$ product:

In another aspect, the present invention relates to a pharmaceutical composition comprising at least one dinucleoside poly(borano)phosphate derivative of the general formula I and a pharmaceutically acceptable carrier or diluent.

The compositions of the invention can be used for prevention or treatment of a disease or disorder modulated by P2-Y receptors.

The disease or disorder modulated by P2-Y receptors may be cancer, a disorder associated with platelet aggregation, a cardiovascular disease or disorder, a disease associated with a disorder of mucous hydration, secretion and clearance, or type 2 diabetes.

The types of cancer that can be treated by the dinucleoside poly(borano)phosphate of the present invention may be, without being limited to, leukemia, lymphoma, multiple myeloma, melanoma, prostate, brain, colon, ovarian, breast, skin, lung, esophagus and bladder cancers.

The cardiovascular disease or disorder may be, without being limited to, ischemia/reperfusion injury, myocardial infarction, and long-standing heart failure.

The diseases associated with a disorder of mucous hydration, secretion and clearance include, without being limited to, chronic obstructive pulmonary disease, pneumonia, bronchitis, cystic fibrosis, primary ciliary dyskinesia, sinusitis, otitis media, dry eye disease, glaucoma, nasolacrimal duct obstruction, edematous retinal disorders, retinal degeneration, vaginal dryness, dry mouth, gastroesophaphageal reflux, and constipation.

As illustrated in Examples 6-8 hereinafter, certain dinucleoside poly(borano)phosphates of the general formula I enhance insulin secretion both in vitro and in vivo, and therefore are candidates for treatment of non-insulin dependent diabetes mellitus (NIDDM) or type 2 diabetes.

The pharmaceutical compositions containing a compound of the present invention may be prepared by conventional techniques, e.g. as described in Remington: The Science and Practice of Pharmacy, 19th Ed., 1995. The compositions may appear in conventional form, for example capsules, tablets, solutions, suspensions, emulsion, cream, spray and the like. The route of administration may be any route which effectively transports the active compound to the appropriate or desired site of action, the oral route being preferred. If a solid carrier is used for oral administration, the preparation may be in the form of a tablet, placed in a hard gelatin capsule in powder or pellet form or it can be in the form of a lozenge. If a liquid carrier is used, the preparation may be in the form of a syrup, emulsion or soft gelatin capsule. Tablets, dragees, or capsules having talc and/or a carbohydrate carrier or binder or the like are particularly suitable for oral application. Preferable carriers for tablets, dragees, or capsules include lactose, corn starch, and/or potato starch. The dosage will be determined by the skilled physician according to the disease, age and condition of the patient.

The invention further relates to a method of preventing, managing or treating a disease or disorder modulated by P2-Y receptors in an individual in need, comprising administering to said individual an effective amount of a dinucleoside poly(borano)phosphate of the general formula I, wherein said amount is sufficient to prevent, manage or treat said disease.

In one embodiment, the disease modulated by P2-Y receptors is type 2 diabetes, and the method of the present invention comprises administering to a diabetic patient in need an effective amount of a dinucleoside poly(borano) phosphate of the general formula I in claim 1, such as the diuridine tri(borano)phosphate $Up_3(\beta-B)U$ tri-sodium salt, wherein said amount is sufficient to treat type 2 diabetes.

The invention will now be illustrated by the following non-limiting Examples.

EXAMPLES

Experimental
(i) General.

All air- and moisture-sensitive reactions were performed in flame-dried, nitrogen flushed, two-neck flasks sealed with rubber septa, and the reagents were introduced with a syringe. Progress of reactions was monitored by TLC on precoated Merck silica gel plates (60F-254). Compounds were characterized by nuclear magnetic resonance using AC-200 spectrometer. $^1$H NMR spectra were measured in $D_2O$, and the chemical shifts are reported in ppm relative to HOD (4.78 ppm) as an internal standard. Dinucleotides were characterized also by $^{31}$P NMR in $D_2O$, using 85% $H_3PO_4$ as an external reference. Dinucleotides were desorbed from a glycerol matrix under FAB (fast atom bombardment) conditions in low and high resolution. Primary purification of the dinucleotides was achieved on an LC (Isco UA-6) system using a Sephadex DEAE-A25 column, which was swelled in 1 M $NaHCO_3$ in the cold for 1 day. Final purification of the nucleotides was achieved on a HPLC (Merck-Hitachi) system using a semipreparative reverse-phase (LiChrospher 60, RP-select-B) column. Conditions for LC and HPLC separation are described below. For analytical purposes, a LiChroCART LiChrospher 60 RP-select B column (250 mm×4 mm) was used with flow rate of 1 ml/min. The purity of the dinucleotides was evaluated on an analytical column in two different solvent systems. One solvent system (I) was (A) $CH_3OH$ and (B) 0.1 M triethylammonium acetate (TEAA), isocratic elution. The second solvent system (II) was (A) 5 mM tetrabutylammonium phosphate (TBAP) in methanol and (B) 60 mM ammonium phosphate and 5 mM TBAP in 90% water/10% methanol, applying an isocratic elution. Apparent pH values were measured with Hanna Instruments pH-meter (HI 8521) equipped with an Orion micro-combination pH electrode (9802). UMP (free acid) and UDP ($Na^+$ salt) were purchased from MP Biochemicals, Inc. $AMP.H_2O$ (free acid) was purchased from Sigma-Aldrich Co. ADP (free acid) was purchased from ICN Biomedicals, Inc.

Example 1

Synthesis of the Boronated Dinucleoside Polyphosphate Derivatives $Ap_3(\beta-B)A$, $Up_3(\beta-B)U$, $Ap_5(\gamma-B)A$ and $Up_5(\gamma-B)U$, 1-4

This example describes the typical procedure for the preparation of boronated dinucleoside polyphosphate derivatives, in particular the diadenosine and diuridine tri (borano)phosphate derivatives $Ap_3(\beta-B)A$ and $Up_3(\beta-B)U$, herein designated compounds 1 and 2, respectively, and the diadenosine and diuridine penta(borano)phosphate derivatives $Ap_5(\gamma-B)A$ and $Up_5(\gamma-B)U$, herein designated compounds 3 and 4, respectively, as the tributylammonium salts, AMP $(Bu_3NH^+)_2$, UMP $(Bu_3NH^+)_2$, ADP $(Bu_3NH^+)_2$ and UDP $(Bu_3NH^+)_2$, respectively.

ADP $(Bu_3NH^+)_2$, AMP $(Bu_3NH^+)_2$ and UMP $(Bu_3NH^+)_2$ were prepared from the corresponding free acid and tributylamine ($Bu_3N$; 2 eq) in EtOH. UDP $(Bu_3NH^+)_2$ was prepared from UDP disodium salt. The latter salt was passed through a column of activated Dowex 50WX-8 200 mesh, $H^+$ form. The column eluate was collected in an ice-cooled flask containing ($Bu_3N$ (2 eq) and EtOH. The resulting solution was freeze-dried to yield UDP $(Bu_3NH^+)_2$ as a viscous oil.

Bis-tributylammonium AMP/UMP/ADP/UDP salt (0.23 mmol) was dissolved in dry dimethylformamide (DMF) (3 ml) and 1,1'-carbonyldiimidazole (CDI) (186.5 mg, 1.15 mmol) was added. The resulting solution was stirred at room temperature for 2.5 h. Dry MeOH (74.6 μl, 1.15 mmol) was added. After 5 min, BPi $(Bu_3NH^+)_2$, 5, (214 mg, 0.46 mmol) in dry DMF (3 ml) and $MgCl_2$ (8 eq) were added. The resulting solution was stirred at room temperature overnight. The semisolid obtained after evaporation of the solvent and was chromatographed at room temperature on a Sephadex DEAE-A25 column, which was swelled in 1M $NaHCO_3$. The separation was monitored by UV detection (ISCO, UA-5) at 280 nm. A buffer gradient of water (800 ml) to 0.7 or 0.5 M $NH_4HCO_3$ (800 ml) was applied. The relevant fractions were pooled and freeze-dried to yield a white solid. Final purification was achieved on a semipreparative HPLC column.

Example 2

Reverse Phase HPLC Purification of Derivatives 1-4

The dinucleotide purification was achieved using a semi-preparative reverse-phase LichroCART 250-10 column and isocratic elution [MeOH: 100 mM triethylammonium acetate (TEAA), pH 7] with flow rate of 6 ml/min. Fractions containing the same compound (similar retention time) were freeze-dried. The excess buffer was removed by repeated freeze-drying cycles dissolving the solid residue each time in deionized water. The triethylammonium counterions were exchanged for $Na^+$ by passing the pure dinucleotide through Sephadex-CM C-25 ($Na^+$-form) column.

$Ap_3(\beta-B)A$, 1 was obtained from AMP $(Bu_3NH^+)_2$ (180 mg, 0.25 mmol) in 88% (90 mg) yield. The final purification was achieved by HPLC, isocratic elution with Methanol: TEAA (13:87). Retention time: 9.46 min. $^1$H NMR ($D_2O$, 200 MHz): δ 8.30 (s, H-8, 1H), 8.07 (s, H-2, 1H), 5.98 (d, H-1', 1H), 4.60 (m, H-2', 1H), 4.48 (m, H-3', 1H), 4.31 (m, H-4', 1H), 4.28 (m, H-5', 2H), −0.9-1.2 (m, $BH_3$, 3H) ppm. $^{31}$P NMR ($D_2O$, 81 MHz, pH 7): δ 78.5 (m, Pβ, 1P), −10.8 (d, Pα, 2P) ppm. HR FAB (negative) calcd for $C_{20}H_{29}^{11}BN_{10}O_{15}P_3$ 753.112, found 753.123 ($M^-$). Retention time: 6.65 min (99% purity) using solvent system I

[(A):(B), 17:83]. Retention time: 5.88 (97% purity) using solvent system II [(A):(B), 23:77].

Up$_3$(β-B)U, 2 was obtained from UMP (Bu$_3$NH$^+$)$_2$ (177.2 mg, 0.255 mmol) in 78% (75 mg) yield. The final purification was achieved by HPLC, isocratic elution with Methanol: TEAA (6:94). Retention time: 6.33 min. $^1$H NMR (D$_2$O, 200 MHz): δ 8.00 (d, J=8.2 Hz, H-5, 1H), 5.99 (d, J=5.1 Hz, H-1', 1H), 5.97 (d, J=8.2 Hz, H-6, 1H), 4.38 (m, H-4', 1H), 4.25 (m, H-5', 2H), −0.90-1.20 (m, BH$_3$, 3H) ppm. $^{31}$P NMR (D$_2$O, 81 MHz, pH 7): δ 75.0 (m, Pβ, 1P), −11.0 (d, Pα, 2P) ppm. HR FAB (negative) calcd for C$_{18}$H$_{27}$$^{11}$BN$_4$O$_{19}$P$_3$ 707.057, found 707.062 (M$^−$). Retention time: 6.86 (98% purity) using solvent system I [(A):(B), 5:95]. Retention time: 8.34 (95% purity) using solvent system II [(A):(B), 10:90].

Ap$_5$(γ-B)A, 3 was obtained from ADP (Bu$_3$NH$^+$)$_2$ (182 mg, 0.228 mmol) in 38% (43 mg) yield. The product was purified by HPLC: isocratic elution with Methanol: TEAA (11:89). Retention time: 9.25 min. $^1$H NMR (D$_2$O, 200 MHz): δ 8.45 (s, H-8, 1H), 8.13 (s, H-2, 1H), 6.00 (d, H-1', 1H), 4.60 (m, H-3', 1H), 4.38 (m, H-4', 1H), 4.30 (m, H-5', 2H), 0-1.30 (m, BH$_3$, 3H) ppm. $^{31}$P NMR (D$_2$O, 81 MHz, pH 7): δ 77.0 (m, Pγ, 1P), −10.5 (d, Pα, 2P), −22.0 (t, Pβ, 2P) ppm. HR FAB (negative) calcd for C$_{20}$H$_{31}$$^{11}$BN$_{10}$O$_{21}$P$_5$ 913.045, found 913.056 (M$^−$). Retention time: 8.71 min (95% purity) using solvent system I [(A):(B), 15:85]. Retention time: 7.85 (95% purity) using solvent system II [(A):(B), 20:80].

Up$_5$(γ-B)U, 4 was obtained from UDP (Bu$_3$NH$^+$)$_2$ (170.5 mg, 0.22 mmol) in 43% (46 mg) yield. The final purification was achieved by HPLC, isocratic elution with Methanol: TEAA (4:96). Retention time: 17 min. $^1$H NMR (D$_2$O, 200 MHz): δ 7.95 (d, J=8.2 Hz, H-5, 1H), 5.99 (d, J=5.1 Hz, H-1', 1H), 5.97 (d, J=8.2 Hz, H-6, 1H), 4.41 (m, H-4', 1H), 4.25 (m, H-5', 2H), −0.90-1.20 (m, BH$_3$, 3H) ppm. $^{31}$P NMR (D$_2$O, 81 MHz, pH 7): δ 77.0 (m, Pγ, 1P), −10.7 (d, Pα, 2P), −22.6 (dd, Pβ, 2H) ppm. HR FAB (negative) calcd for C$_{18}$H$_{28}$$^{11}$BN$_4$O$_{25}$Na$_2$P$_3$ 910.965, found 910.966 (M−2H+2Na)$^−$. Retention time: 6.70 min (98% purity) using solvent system I [(A):(B), 6:94]. Retention time: 6.17 (99% purity) using solvent system II [(A):(B), 12:88].

Example 3

Evaluation of Chemical Stability of Derivatives 1-4

To explore the suitability of the new P2Y-R agonists 1-4 as drug candidates for oral administration, we evaluated their hydrolytic stability. As depicted in Scheme 3, Np$_n$(B)N analogues may undergo several hydrolytic pathways: (A) Hydrolytic cleavage of the phosphodiester bond at Pα, to produce the free nucleoside (N) and Np$_n$(-β/γ-B). (B) Hydrolytic cleavage of the phosphodiester bond at Pβ, to release Np$_{n-1}$(-β/γ-B) and NMP. (C) Hydrolytic cleavage of the phosphodiester bond at the central boranophosphate moiety, Pβ/Pγ, to release Np$_{2/3}$(-β/γ-B) and Np$_{1/2}$. (D) Hydrolytic cleavage of the phosphodiester bond at the central boranophosphate moiety, Pβ/Pγ, to release BPi and two molecules of Np$_{1/2}$.

The stability of compounds 1-4 in the appropriate buffer solutions (pH 7.4 or 1.4) was evaluated at 37° C. $^{31}$P NMR was used for monitoring phosphate-chain degradation products. Dinucleosides poly(borano)phosphates tri- or penta-sodium salts were dissolved in Tris/HCl buffer (pH 7.4, 0.45 ml), and D$_2$O (0.6 ml). pH 7.4 was then adjusted with HCl and measured with a pH-meter. Final analogue concentration was about 0.02 M. $^{31}$P NMR spectra were recorded during 4 weeks at 3-7 days intervals at 37° C. Percentage of phosphoester hydrolysis of Ap$_3$(β-B)A/Up$_3$(β-B)U is based on absolute integrations of monophosphate signal (2.5 ppm). Percentage of phosphodiester hydrolysis of dinucleoside pentaphosphate is based on absolute integrations of Pα signal of ADP or UDP products.

To evaluate chemical stability at pH 1.4, sodium salts of dinucleoside poly(borano)phosphate analogues were dissolved in KCl/HCl buffer (pH 1.4, 0.44 ml) and D$_2$O (0.06 ml). The final pH was then adjusted with HCl and measured with a pH-meter (final concentration 0.016 M). $^{31}$P NMR spectra of Ap$_3$(β-B)A and Up$_3$(β-B)U were recorded during 3 h at 10 min time intervals at 37° C. Number of scans in all experiments was 1200, number of experiments was 17. The hydrolysis rate was determined by measurements of absolute integration of Pα (2.5 ppm) signal as a function of time and was fitted to a pseudo-first-order reaction model.

$^{31}$P NMR spectra of Ap$_5$(β-B)A was recorded during 1 h at 10 min time intervals at 37° C. Number of scans in all experiments was 1200, number of experiments was 6. The hydrolysis rate was determined by measurement the absolute intagration of Pβ signal as a function of time and was fitted to a pseudo-first-order reaction model.

Chemical stability under conditions simulating gastric juice (pH 1.4/37° C.) was evaluated with Ap$_3$(β-B)A, 1, Up$_3$(β-B)U, 2, and Ap$_5$(γ-B)A, 3 sodium salts, in KCl/HCl buffer. $^{31}$P NMR spectra was recorded during 3 h at 10 min intervals. For compounds 1 and 2, increasing amounts of AMP/UMP were observed in addition to starting material 1 or 2. However, $^{31}$P NMR spectrum did not show in addition a quartet at about 95 ppm typical of protonated inorganic Bpi (Nahum and Fischer, 2004). Mass spectrometric analysis (FAB negative) of the hydrolytic mixture of 1 after neutralization shows that hydrolysis does not occur symmetrically to produce two AMP/UMP molecules and one Bpi. Instead, hydrolysis occurs at Pβ position to provide one AMP/UMP molecule and one ADP/UDP-β-B molecule. Although the signals of ADP/UDP-β-B were hidden by the signals of Pβ and Pα of compounds 1/2, mass spectrometric analysis revealed that the hydrolytic mechanism of analogues 1 and 2 is asymmetric corresponding to path C in Scheme 3. The signal for the nucleoside monophosphate (1 ppm) gradually increased. The intensity changes of the monophosphate $^{31}$P signal with time were fit to a pseudo first-order exponential decay rate equation with respect to 1/2 concentration. The calculated hydrolysis rate constant determined at pH 1.4/37° C. for 1 and 2 were $1.52 \times 10^{-4}$ sec$^{-1}$ and $1.65 \times 10^{-4}$ sec$^{-1}$, respectively, corresponding to t$_{1/2}$ of 1.3 and 1.2 h.

The major difference between the $^{31}$P NMR chemical shifts of borano-phosphates and phosphates, about 90 ppm, enables easy monitoring of the above mentioned degrading reactions by $^{31}$P NMR spectroscopy.

The effect of the borane group on the hydrolytic stability of Np$_n$(B)N analogues was monitored at physiological conditions, pH 7.4/37° C., and conditions simulating gastric juice, pH 1.4/37° C. Thus, $^{31}$P NMR spectra of Up$_3$(β-B)U, 2, and Ap$_5$(β-B)A, 3, tri- and penta-sodium salts, respectively, in Tris/HCl buffer (in H$_2$O), pH 7.4, were recorded during 4 weeks at 1- to 3-day intervals at 37° C. Under these conditions, compounds 2 and 3 exhibited unusual stability. The decomposition of compound 3 was less than 15% as judged by the signal for Pα of ADP product at 2.5 ppm, and no decomposition at all was observed for compound 2. No deboranation products could be detected.

A preferential nucleophilic attack on the boranophosphate moiety at pH 1.4 was observed for compounds 1 and 2. Likewise, the attack on the α-boranophosphate—the "weak spot"—of the phosphate chain, was observed also for ATP-α-B yielding BPi, PPi and nucleoside (Nahum et al., 2002).

The higher stability of analogues 1-4 at pH 7.4 vs. 1.4 is due to the predominant existing polyanion form that retards the nucleophilic attack of a water molecule.

The base, either adenine or uracil, does not affect the hydrolytic stability of analogues 1-4. Yet, the length of the polyphosphate chain in these analogues makes a difference. $Ap_5(\gamma\text{-B})A$ is about 4-fold less hydrolytically stable as compared to its lower homologue, $Ap_3(\beta\text{-B})A$. $Ap_3(\beta\text{-B})A$ in turn is slightly (2-fold) less stable than ATP-α-B analogues we studied before under gastric juice conditions (Nahum et al., 2002).

However, under physiological conditions, both $Up_3(\beta\text{-B})U$ and $Ap_3(\beta\text{-B})A$ are by far more stable than ATP-α-B analogues ($t_{1/2}$ of the latter is about 1400 h), showing no decomposition even after one month. This extreme hydrolytic stability of $Ap_3(\beta\text{-B})A$ and $Up_3(\beta\text{-B})U$, and the high stability of $Ap_5(\gamma\text{-B})A$ (less than 10% decomposition after 1 month) may be due to the lack of a terminal phosphate.

However, ATP-α-B analogues having a partially protonated terminal phosphate are more susceptible to nucleophilic attack by water.

Scheme 1: General procedure for the preparation of Bpi, 5

Scheme 2: Typical procedure for the preparation of compounds 1-4

Scheme 3. Possible hydrolytic pathways of compounds 1–4

A = adenine

Example 4

Synthesis of Dinucleoside Tri(borano)phosphate Derivatives Boronated at Two or Three Positions The synthesis of dinucleoside tri(borano)phosphate derivatives boronated at two or three positions is carried out as exemplified herein for the uridine derivatives Up$_3$(α,γ-B)U and Up$_3$(α,β,γ-B)U.

(i) Preparation of intermediate 2',3'-O-methoxymethylidene uridine.

p-TsOH (2 mmol, 2 eq) was added to dry uridine (1 mmol, 1 eq) in a two-neck flask under $N_2$, followed by addition of dry DMF (4 ml). Then, trimethylorthoformate (50 eq) was added and the resulting solution was stirred at room temperature for 1 day. The mixture was cooled to 0° C. and Dowex MWA-1 (weakly basic anion exchanger, 6 eq) was added. Stirring continued at room temperature for additional 3 h. The Dowex resin was filtered out in vacuo; the filtrate was concentrated under reduced pressure and coevaporated several times with MeOH to remove residual DMF. The residue was dissolved in $CHCl_3$ and extracted with saturated $NaHCO_3$. The organic phase was dried with $Na_2SO_4$ and evaporated to give pure 2',3'-O-methoxymethylidene uridine.

(ii) Preparation of derivatives of uridine-5'-O-(Pα-borano) monophosphate.

The protected uridine derivative of step (i) above (0.5 mmol) was dissolved in dry $CHCl_3$ (7 ml) in a flame-dried, two-neck flask under $N_2$. $(iPr)_2NEt$ (0.11 ml, 1.3 eq) was added at room temperature and the solution was stirred for 30 min. The mixture was cooled to 0° C. and $[(iPr)_2N]_2PCl$ (148 mg, 1.1 eq), dissolved in $CHCl_3$ (2 ml), was slowly added with a syringe. The resulting solution was stirred at 0° C. for 2 h followed by the addition of a 2 M solution of $BH_3.SMe_2$ complex in THF (2.52 ml, 10 eq) at 0° C. After 15 min of stirring at room temperature, deionized water (8 ml) was added and the resulting mixture was stirred for 1 h and then freeze-dried. The product was dissolved in water and extracted with $CHCl_3$. The aqueous phase was freeze-dried and the resulting residue was applied on an activated Sephadex DEAE-A25 column (0-0.7 M $NH_4HCO_3$, total volume>2000 ml). The relevant fractions were collected and freeze-dried; excess $NH_4HCO_3$ was removed by repeated freeze-drying with deionized water to yield the product as the bis(ammonium) salt. The methoxymethylidene protecting group was removed by acidic hydrolysis (10% HCl solution was added till pH 2.3 was obtained). After 3 h at room temperature, the pH was rapidly raised to 9 by the addition of $NH_4OH$ solution (pH 11) and the solution was kept at room temperature for 40 min. The desired uridine-5'-O-(1-boranomonophosphate) derivative was obtained after freeze-drying of the solution. Final purification was achieved on a semipreparative HPLC column.

The obtained product is used for the preparation of $Up_3(\alpha,\gamma-B)U$ and $Up_3(\alpha,\beta,\gamma-B)U$ following the procedure described in Example 1 above.

Example 5

Analyzing the Biological Activity of the Dinucleosides Poly(borano)phosphate Derivatives In general, the pharmacological activity of the dinucleosides poly(borano)phosphate derivatives of the invention can be tested by calcium elevation measurements of cells expressing the P2Y2-R (Tulapurkar et al., 2005) or any relevant P2Y-R (Vöhringer et al., 2000) affected by varying concentrations of the said compounds. Briefly, the changes in free intracellular $Ca^{2+}$ concentration ($[Ca^{2+}]_i$) are measured, as described by Ubl et al (1998), after pre-incubation of the cells with 2 μM Fura-2AM for 30 min in NaHBS (HEPES buffered saline solution: 145 mM NaCl, 5.4 mM KCl, 1.8 mM $CaCl_2$, 1 mM $MgCl_2$, 25 mM glucose and 20 mM HEPES/Tris pH 7.4). The cells are then stimulated under continuous superfusion of pre-warmed NaHBS at 37° C. with different concentrations of the different dinucleoside poly(borano)phosphate analogue at 37° C. Fluorescence intensity is recorded alternately at 340 and 380 nm excitation and 520 nm emission (Tulapurkar et al., 2004).

The pharmacological activity of the dinucleosides poly (borano)phosphate derivatives of the invention may also be tested as described in U.S. Pat. No. 6,596,725, herein incorporated by reference in its entirety as if fully disclosed herein. The initial test is the inositol phosphate assay for $P2Y_2$ receptor, a receptor known to be equipotently activated by both ATP and UTP (Lazarowski et al., 1995) and to activate phospholipase C. The $P2Y_2$ receptor exhibits a broad tissue distribution. For example, activation of $P2Y_2$ receptors on human airway epithelial cells promotes chloride secretion and this receptor represents, therefore, a therapeutically important target in human airway disease such as cystic fibrosis.

The inositol phosphate assay for $P2Y_2$ receptor relies on the measurement of inositol phosphate formation as a measurement of activity of compounds activating receptors linked via G-proteins to phospholipase C.

The cells used in the inositol phosphate accumulation assay may be human P2Y purinergic receptor expressing cells such as the 1321N1 human astrocytoma cells (Lazarowski et al., 1995). In a typical assay, confluent cells are incubated overnight in 0.2 ml of serum-free, inositol-free, phenol red-free RPMI (or inositol-free DMEM containing glucose) containing myo-[$^3$H]inositol (14 Ci/mmol). Assays are carried out on the following day after equilibration with 50 mM HEPES, pH 7.4, for 60 min. LiCl (15 mM), a inositol phosphate inhibitor, is added to each well 10 min before the addition of the candidate agonist. Reactions are terminated by adding an equal volume of 10% trichloroacetic acid to lyse the cells and release [$^3$H]inositol phosphates. Samples are extracted with ethyl ether to remove the trichloroacetic acid. [$^3$H]Inositol phosphates are separated by anion exchange chromatography on Dowex AG1-X8 columns and quantified by liquid scintillation counting.

The formation and accumulation rate of [$^3$H] inositol phosphate promoted by the tested compound in comparison to the basal level indicates that the tested compound is a P2Y receptor agonist and a potential candidate for treatment of diseases of the airway tissues, as described herein in the application. The efficacy of the potential candidates can then be tested in animal models, for example, as described in the above-mentioned U.S. Pat. No. 6,596,725. The dinucleoside poly(borano)phosphate derivatives of the general formula I herein are expected to be active in the inositol phosphate assay and in the in vivo assays.

Example 6

Glucose-Dependent Stimulation of Insulin Secretion in INS-1 Cells by the diuridine-tri(borano)phosphate trisodium salt Compound 2, sodium salt, was tested for insulinotropic effect on insulin-secreting INS-1 cells (Hohmeier et al., 2000). Briefly, the cells were plated at a density of $2 \times 10^5$ in 12-well plates in RPMI with 10% fetal calf serum containing 11 mM glucose and maintained at 37° C. in a humidified atmosphere containing 5% $CO_2$ for 2 days. The medium was removed on the third day post-plating and replaced with RPMI containing 3 mM glucose with 10% fetal calf serum. The cells were incubated for an additional 24 hours at 37° C. in a humidified atmosphere containing 5% $CO_2$. On the fourth day post-plating, the medium was removed and replaced with Krebs-Ringer bicarbonate Hepes buffer (pH 7.4) containing 2 mM glucose. The cells were incubated for 30 min, and then the buffer was removed and replaced with Krebs-Ringer bicarbonate Hepes buffer (pH 7.4) with 6 mM glucose containing the test compound at various concentrations. The cells were incubated for 1 hour. Basal insulin secretion was determined by incubating the cells in the presence of buffer with 2 mM glucose. The presence of glucose at 6 and 10 mM stimulated insulin secretion and served as the reference control and positive control, respectively. A positive stimulatory response by the test compound was taken as the response above that elicited by 6 mM glucose.

Figure 1:
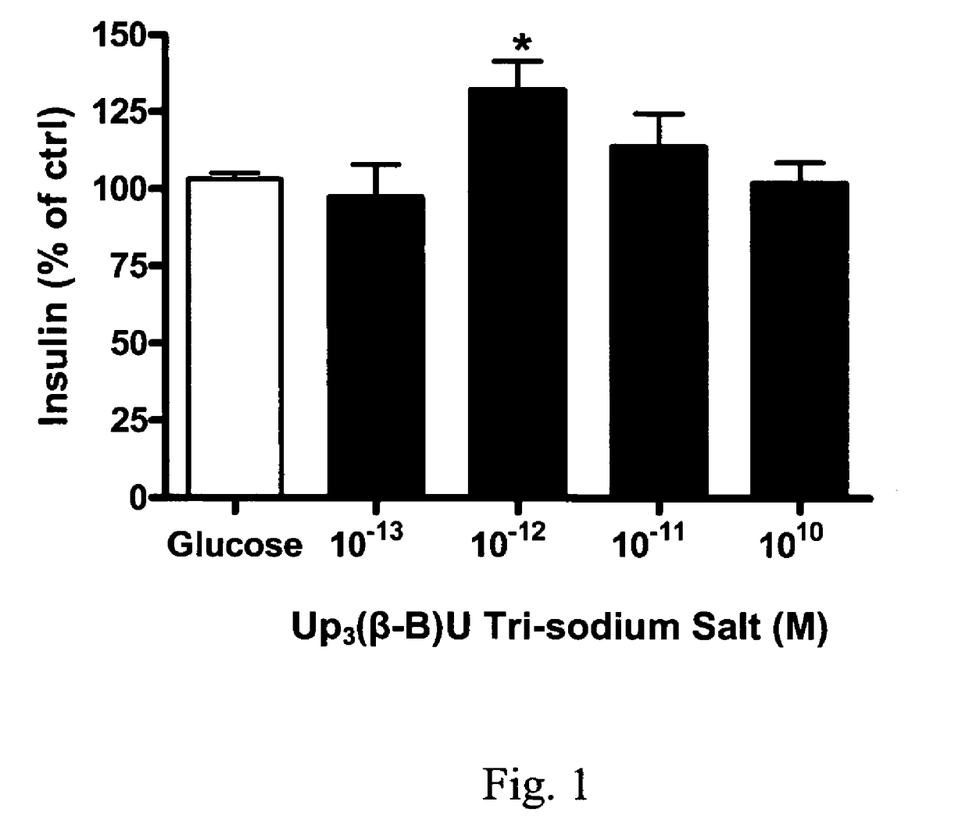
FIG. 1 shows the insulin secretion level in INS-1 cells induced by various concentrations of diuridine poly(borano)phosphate ($Up_3(\beta$-B)U) tri-sodium salt.

As illustrated in FIG. 1, diuridine-tri(borano)phosphate trisodium salt VN-54 stimulated insulin secretion above background levels. The compound was active at low concentrations ($10^{-12}$ and $10^{-11}$ M) with activity dropping as the concentration increased.

Example 7

Glycemic Response of Diet-Induced Obesity (DIO)-Mice Following a Single Intravenous Administration of diuridine-tri(borano)phosphate trisodium salt, 2, at 1 Minute Prior to Oral Glucose Tolerance Test The ability of the diuridine-tri(borano)phosphate trisodium salt, 2, to modulate glycemia was demonstrated in vivo using an hyperglycemic mouse model known as the Diet-Induced Obesity (DIO) mouse model.

C57BL/6 male mice (Charles River Canada, St-Constant, Qc, Canada) were received at 7-8 weeks of age and fed a high fat diet (60% of calories from fat) for 6-8 weeks to induce hyperglycemia and obesity (Surwit et al., 1988). Blood glucose was checked and animals with readings between 200 and 220 mg/dl were included in the study. The animals were randomized based on their body weight and glycemic values, into control and treatment groups (n=6-8). The animals received a single intravenous injection of the test compound one minute prior to the Oral Glucose Tolerance Test (OGTT). The control group received vehicle (saline) alone. Blood samples (one drop) were collected from the tail vein prior to the administration of the test compound and at 5, 10, 20, 30, 60, 90 and 120 minutes post-glucose administration. Whole blood glucose values were determined using a hand-held glucometer (Model OneTouch Ultra, LifeScan). All data are expressed as mean±SEM.

Figure 2A:
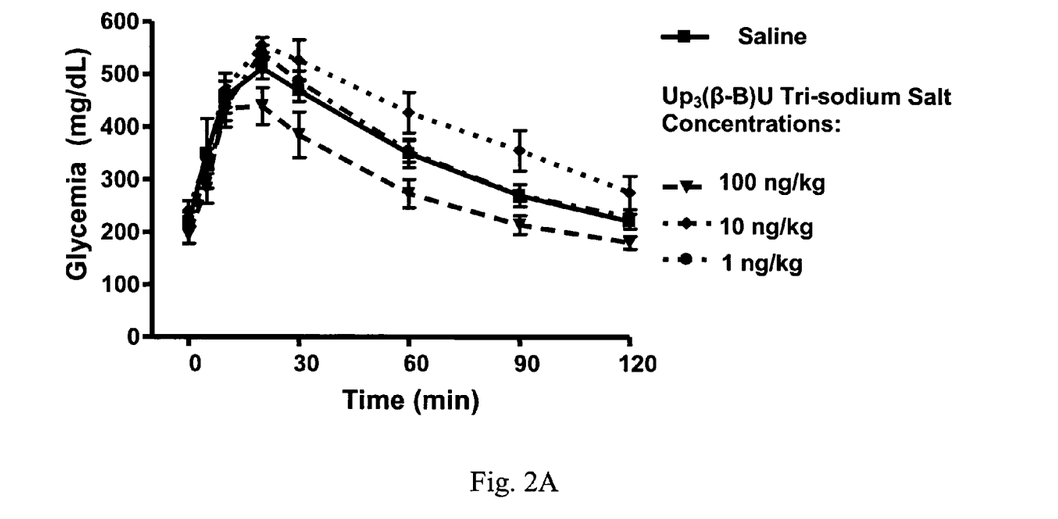
FIGS. 2A-2B show the delta glycemia (2A) and the area under the curve (AUC) of delta glycemia (2B) induced by various concentrations of $Up_3(\beta$-B)U tri-sodium salt, using the Diet-Induced-Obesity (DIO) mouse model.
Figure 2B:
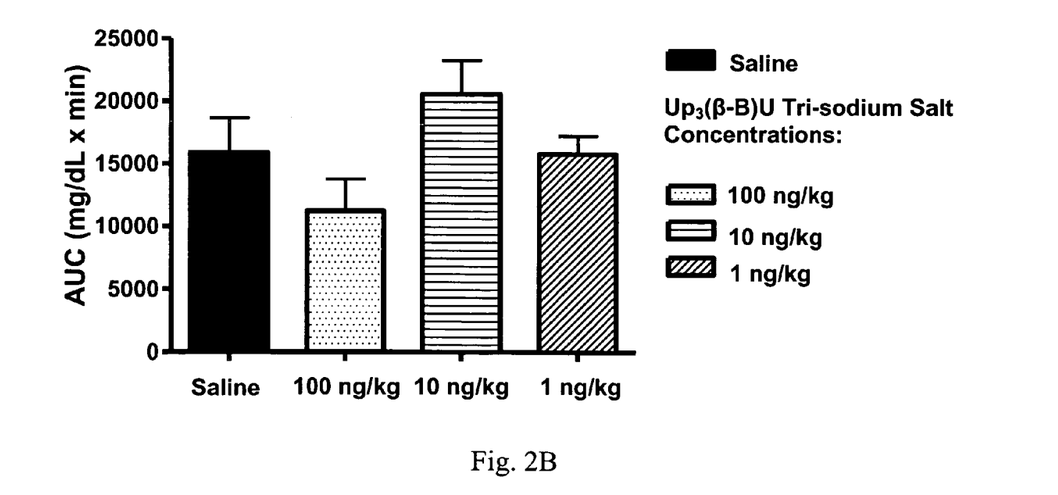

FIG. 2 is an area under the curve (AUC) graph of delta glycemia. It is a representation of the area under the curve of the responses seen during the oral glucose tolerance test challenge. The data are corrected for the baseline blood glucose levels of the individual mice. When given a bolus of glucose, glucose levels rise in the blood and, depending on the efficiency of insulin secretion, glucose levels will return to baseline levels over a period of 2 to 3 hours. The graph shows that animals receiving saline took longer to return to normal than animals treated at 100 ng/kg with VN-54. If the area under the curves is integrated, the response can be quantified as represented in the bar graph. The results in FIG. 2 show that VN-54 partially inhibited the increase of the glycemia of DIO-mice when administered one minute prior to the glucose challenge. The compound was active at low concentration (100 ng/kg) with activity dropping as the concentration decreased.

Example 8

Effect of the P2Y Receptor Agonist, 2, sodium salt, on Insulin Secretion using Human Islets The objective of these experiments was to determine the relative activity of various borano-substituted P2Y receptor agonists on insulin secretion when incubated with human islets in the presence of various concentrations of glucose.

Islets were kept in CMRL 1066 medium containing 5.5 mM glucose for 2-3 days and then washed out with medium containing 2.2 mM glucose. Islet aliquots were supplemented with 1 ml of medium containing 2.2, 12 or 22 mM glucose or 22 mM glucose with 3-isobutyl-1-methylxanthine (IBMX), in the presence or absence of the different secretagogues. The experiments were done in triplicate. Islets were incubated for 30 minutes at 37° C. in a humidified atmosphere containing 5% $CO_2$. After incubation, the medium was collected for determination of insulin level. Quantification of insulin was done in duplicate using human insulin ELISA kit (ALPCO). Islets were collected for determination of protein using the Bradford assay so that insulin secretion could be normalized to total protein. Basal insulin secretion was determined by incubating the islets in the presence of buffer with 2 mM glucose. The presence of glucose at 12 and 22 mM stimulated insulin secretion and served as the reference controls while the presence of 22 mM with IBMX served as positive control. A positive stimulatory response by the compounds was taken as the response above that elicited by reference controls.

Figure 3:
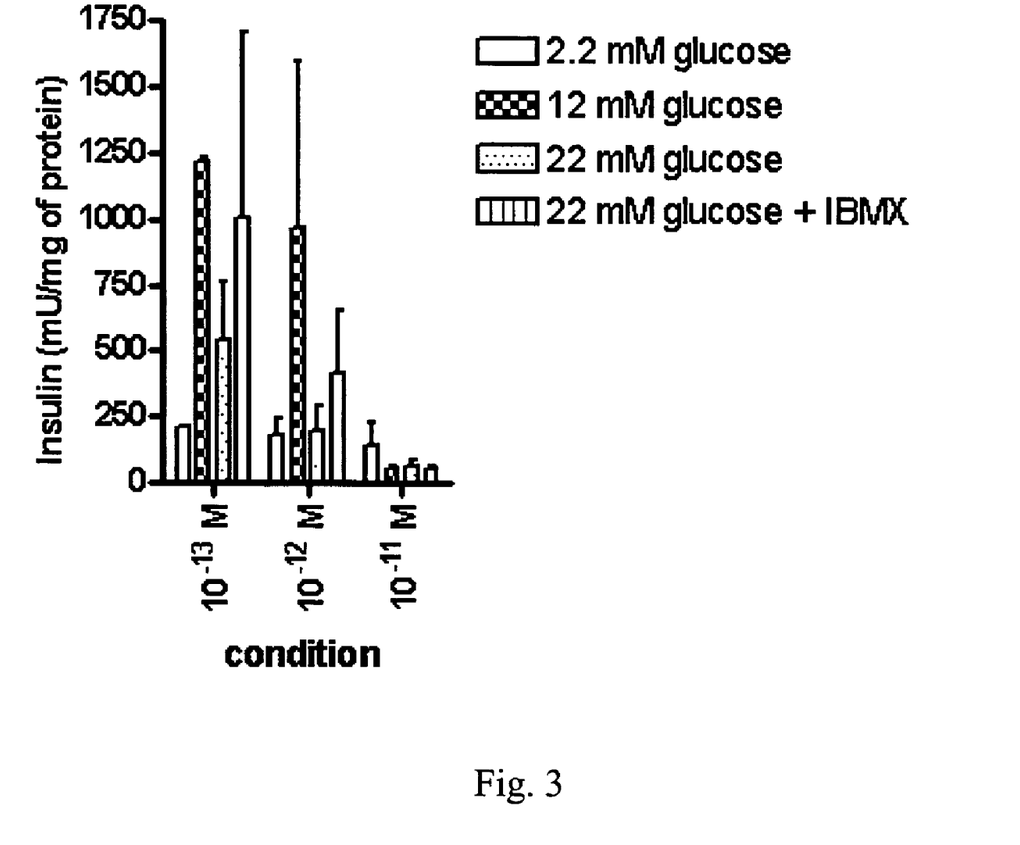

As illustrated in FIG. 3, under conditions of 12 mM glucose, diuridine poly(borano)phosphate tri-sodium salt at $10^{-13}$ and $10^{-12}$ M was able to promote significant insulin secretion by human islets.

REFERENCES

Chambers, R. W.; Moffatt, J. G.; Khorana, H. G., *J. Am. Chem. Soc.,* 1957, 79, 3747-3752

Fischer, B., *Exp. Opin. Therap. Pat.,* 1999, 9, 385-399

Fischer, B. Chulkin, A. Boyer, J. L. Harden, K. T. Gendron, F. P. Beaudoin, A. R. Chapal, J. Hillaire-Buys, D. Petit, P., *J. Med. Chem.,* 1999, 42, 3636-3646

Garrison, P. N. de la Pena, C. E. Barnes, L. D., *Anal. Biochem.,* 1993, 210, 226-230

Goldman, L. Marsico, J. W. Anderson, G. W., *J. Am. Chem. Soc.,* 1960, 82, 2969-2970

Hillaire-Buys, D. Bertrand, G. Chapal, J. Puech, R. Ribes, G. Loubatières-Mariani, M. M., *Br. J. Pharmacol.,* 1993, 109, 183-187

Hoard, D. E. Ott, D. G., *J. Am. Chem. Soc.,* 1965, 87, 1785

Hohmeier, H. E. Mulder, H. Chen, G. Henkel-Ringer, R. Prentki, M. Newgard, C. B., *Diabetes,* 2000, 49, 424-430

Kadokura, M. Wada, T. Urachima, C. Sekine, M., *Tet. Let.,* 1997, 38, 8359-8362

Lazarowski, E. R. Watt, W. C. Stutts M. J. Boucher, R. C. Harden, T. K., *Brit. J Pharm.,* 1995, 116, 1619-1627

Moffat, J. G., *Can. J. Chem.,* 1964, 42, 599

Nahum, V. Fischer, B., *Eur. J. Inorg. Chem.,* 2004, 20, 4124-4131

Nahum, V. Zuendorf, G. Levesque, S. A. Beaudoin, A. R. Reised, G. Fischer, B., *J. Med. Chem.,* 2002, 45(24), 5384-5396

Ribes, G. Bertrand, G. Petit, P. Loubatières-Mariani, M. M., *Eur. J. Pharmacol.,* 1988, 155, 171-174

Sawai, H. Shimazu, M. Wakai, H. Wakabayashi, H. Shinozuka, K., *Nucleosides and Nucleotides,* 1992, 11, 773-785

Shimazu, M. Shinozuka, K. Sawai, H., *Tet. Let.*, 1990, 31, 235-238

Tulapurkar, M. E. Laubinger, W. Nahum, V. Fischer, B. Reiser, G., *Br. J. Pharmacol.*, 2004, 142, 821-830

Tulapurkar, M. E. Schafer, R. Hanck, T. Flores, R. V. Weisman, G. A. Gonzalez, F. A. Reiser, G., *Cell Mol Life Sci.*, 2005, 62(12), 1388-1399

Ubl, J. J. Vohringer, C. Reiser, G., *Neuroscience*, 1998, 86, 597-609

Vohringer, C. Schafer, R. Reiser, G., *Biochem Pharmacol.*, 2000, 59(7), 791-800

Zatorski, A., *J. Med. Chem.*, 1995, 38, 1098-1105

The invention claimed is:

1. A diribo-, di-2'-deoxyribo-, or ribo-2'-deoxyribo-nucleoside boranophosphate derivative of the general formula I:

wherein

X and X' each independently is a purine residue of the formula Ia, linked through the 9-position:

wherein

$R_1$ is selected from the group consisting of H, halogen, O-hydrocarbyl, S-hydrocarbyl, $NR_4R_5$, heteroaryl, unsubstituted hydrocarbyl and hydrocarbyl substituted by halogen, CN, SCN, $NO_2$, $OR_4$, $SR_4$, $NR_4R_5$ or heteroaryl, wherein $R_4$ and $R_5$ each independently is H or hydrocarbyl or $R_4$ and $R_5$ together with the nitrogen atom to which they are attached form a 5- or 6-membered saturated or unsaturated heterocyclic ring optionally containing 1-2 further heteroatoms selected from the group consisting of oxygen, nitrogen and sulfur, the additional nitrogen being unsubstituted or substituted by alkyl substituted by halogen, hydroxyl or phenyl;

$R_2$ is H or absent;

$R_3$ is O or $NHR_6$ wherein $R_6$ is H or hydrocarbyl; and the dotted line represents a potential double bond between the carbon atom at position 6 and either the nitrogen atom at position 1 or the radical $R_3$, provided that, when $R_2$ is H, there is a double bond between the carbon atom at position 6 and $R_3$, and when $R_2$ is absent, there is a double bond between the carbon atom at position 6 and the nitrogen atom at position 1;

or X and X' each independently is a pyrimidine residue of the formula Ib, linked through the 1-position:

wherein $R_7$ and $R_8$ each independently is H, halogen, O-hydrocarbyl, S-hydrocarbyl, $NR_{11}R_{12}$, heteroaryl, unsubstituted hydrocarbyl or hydrocarbyl substituted by halogen, CN, SCN, $NO_2$, $OR_{11}$, $SR_{11}$, $NR_{11}R_{12}$ or heteroaryl, wherein $R_{11}$ and $R_{12}$ each independently is H or hydrocarbyl or $R_{11}$ and $R_{12}$ together with the nitrogen atom to which they are attached form a 5- or 6-membered saturated or unsaturated heterocyclic ring optionally containing 1-2 further heteroatoms selected from the group consisting of oxygen, nitrogen and sulfur, the additional nitrogen being unsubstituted or substituted by alkyl substituted by halogen, hydroxyl or phenyl;

$R_9$ is O or $NHR_{13}$ wherein $R_{13}$ is H or hydrocarbyl;

$R_{10}$ is H or absent; and the dotted line represents a potential double bond between the carbon atom at position 4 and either the nitrogen atom at position 3 or the radical $R_9$, provided that, when $R_{10}$ is H, there is a double bond between the carbon atom at position 4 and $R_9$, and when $R_{10}$ is absent, there is a double bond between the carbon atom at position 4 and the nitrogen atom at position 3;

wherein any said hydrocarbyl in any $R_1$ to $R_{13}$ is a radical containing only carbon and hydrogen atoms that may be saturated or unsaturated, linear or branched, cyclic or acyclic, or aromatic, and includes $C_1$-$C_8$ alkyl, $C_2$-$C_8$ alkenyl, $C_2$-$C_8$ alkynyl, $C_3$-$C_{10}$ cycloalkyl, $C_3$-$C_{10}$ cycloalkenyl, $C_6$-$C_{14}$ aryl, $(C_1$-$C_8)$alkyl$(C_6$-$C_{14})$aryl, and $(C_6$-$C_{14})$aryl$(C_1$-$C_8)$alkyl;

Y and Y' each independently is H or OH;

$Z_1$, $Z_2$, $Z_3$, $Z_4$ and $Z_5$ each independently is $O^-$ or $BH_3^-$, but excluding the compounds wherein Z1 to Z5 are each $O^-$;

$W_1$, $W_2$, $W_3$ and $W_4$ each independently is O, $CH_2$, NH or $C(Hal)_2$, wherein Hal is halogen, preferably F or Cl;

n and n' each independently is 0 or 1;

m is 3, 4 or 5; and $M^+$ represents a pharmaceutically acceptable cation and the diastereoisomers thereof; formed by variations in the location of the $BH_3$ moieties.

2. The dinucleoside boranophosphate derivative of claim 1, wherein n and n' are 1, $W_1$ to $W_4$ are O, and at least one of $Z_1$ to $Z_5$ is $BH_3^-$; or n is 0 and n' is 1, $W_2$ to $W_4$ are O, and at least one of $Z_1$ and $Z_3$ to $Z_5$ is $BH_3^-$; or n and n' are 0, $W_2$ and $W_3$ are O, and at least one of $Z_1$, $Z_3$ and $Z_5$ is $BH_3^-$.

3. The dinucleoside boranophosphate derivative of claim 2, wherein n and n' are 1, comprising a sole borano group at position α (or α'), namely, $Z_1$ (or $Z_5$) is $BH_3^-$ and $Z_2$, $Z_3$, $Z_4$ and $Z_5$ (or $Z_1$) are $O^-$; at position β (or β'), namely, $Z_2$ (or $Z_4$) is $BH_3^-$ and $Z_1$, $Z_3$, $Z_5$ and $Z_4$ (or $Z_2$) are $O^-$; or at position γ, namely, $Z_3$ is $BH_3^-$ and $Z_1$, $Z_2$, $Z_4$ and $Z_5$ are $O^-$, two borano groups at positions α,β (or α',β'), namely, $Z_1$ and $Z_2$ (or $Z_4$ and $Z_5$) are $BH_3^-$ and $Z_3$, $Z_4$ and $Z_5$ (or $Z_1$, $Z_2$ and $Z_3$) are $O^-$; at positions β,γ (or β',γ), namely, $Z_2$ and $Z_3$ (or $Z_3$ and $Z_4$) are $BH_3^-$ and $Z_1$, $Z_4$ and $Z_5$ (or $Z_1$, $Z_2$ and $Z_5$) are $O^-$; at positions α,γ (or α',γ), namely, $Z_1$ (or $Z_5$) and $Z_3$ are $BH_3^-$ and $Z_2$, $Z_4$ and $Z_5$ (or $Z_1$) are $O^-$; at positions α,β' (or α',β), namely, $Z_1$ and $Z_4$ (or $Z_2$ and $Z_5$) are $BH_3^-$ and $Z_2$, $Z_3$ and $Z_5$ (or $Z_1$, $Z_3$ and $Z_4$) are $O^-$; at positions α,α' ($Z_1$, $Z_5$); or at positions β,β' ($Z_2$, $Z_4$), or three borano groups at positions α,β,γ (or α',β',γ), namely, $Z_1$, $Z_2$, and $Z_3$ (or $Z_5$, $Z_4$ and $Z_3$) are $BH_3^-$ and $Z_4$ and $Z_5$ (or $Z_1$ and $Z_2$) are $O^-$; at positions α,β,α' ($Z_1$, $Z_2$, $Z_5$); at positions α,β,β' ($Z_1$, $Z_2$, $Z_4$); at positions α',β,β' ($Z_2$, $Z_4$, $Z_5$); at positions α,α',β' ($Z_1$, $Z_4$, $Z_5$); at positions α',β,γ ($Z_2$, $Z_3$, $Z_5$); at positions α,β',γ ($Z_1$, $Z_3$, $Z_4$); or at positions β,γ,β' ($Z_2$, $Z_3$, $Z_4$).

4. The dinucleoside boranophosphate derivative of claim 2, wherein n is 0 and n' is 1, comprising a sole borano group at position α (or α'), namely, $Z_1$ (or $Z_5$) is $BH_3^-$ and $Z_3$, $Z_4$ and $Z_5$ (or $Z_1$) are $O^-$; or at position β (or β'), namely, $Z_3$ (or $Z_4$) is $BH_3^-$, and $Z_1$, $Z_4$ (or $Z_3$) and $Z_5$ are $O^-$, two borano groups at positions α,β (or α', β'), namely, $Z_1$ and $Z_3$ (or $Z_4$ and $Z_5$) are $BH_3^-$ and $Z_4$ and $Z_5$ (or $Z_1$ and $Z_3$) are $O^-$; at positions β,β', namely, $Z_3$ and $Z_4$ are $BH_3^-$ and $Z_1$ and $Z_5$ are $O^-$; at positions α,α' ($Z_1$, $Z_5$); at positions α,β' ($Z_1$, $Z_4$); or at positions (α',β), or three borano groups at positions α,β,β' (or α',β,β'), namely, $Z_1$, $Z_3$ and $Z_4$ (or $Z_5$, $Z_4$ and $Z_3$) are $BH_3^-$ and $Z_5$ (or $Z_1$) is $O^-$; at positions α,α',β ($Z_1$, $Z_3$, $Z_5$); or at positions α,α',β' ($Z_1$, $Z_4$, $Z_5$).

5. The dinucleoside boranophosphate derivative of claim 2, wherein n and n' are 0, comprising a sole borano group at position α (or α'), namely, $Z_1$ (or $Z_5$) is $BH_3^-$ and $Z_3$ and $Z_5$ (or $Z_1$) are $O^-$; or at position β, namely, $Z_3$ is $BH_3^-$ and $Z_1$ and $Z_5$ are $O^-$, two borano groups at positions α,β (or α',β), namely, $Z_1$ (or $Z_5$) and $Z_3$ are $BH_3^-$ and $Z_5$ (or $Z_1$) is $O^-$; or at positions α,α' ($Z_1$, $Z_5$), or three borano groups at positions α,β,α', namely, $Z_1$, $Z_3$ and $Z_5$ are $BH_3^-$.

6. The dinucleoside boranophosphate derivative of claim 1, wherein X and X' are a purine residue, wherein $R_1$ is H, $R_2$ is absent, and $R_3$ is $NH_2$; Y and Y' are OH; $Z_1$, $Z_2$, $Z_4$ and $Z_5$ are $O^-$; $Z_3$ is $BH_3^-$; $W_1$, $W_2$, $W_3$ and $W_4$ are O; and either n and n' are 0 and m is 3, or n and n' are 1 and m is 5.

7. The dinucleoside boranophosphate derivative of claim 1, wherein X and X' are a purine residue, wherein $R_1$ is H, halogen, O-hydrocarbyl or S-hydrocarbyl.

8. The dinucleoside boranophosphate derivative of claim 1, wherein X and X' are a purine residue, wherein $R_1$ is H or $NR_4R_5$, and $R_4$ and $R_5$ each independently is H or hydrocarbyl or $R_4$ and $R_5$ together with the nitrogen atom to which they are attached form a saturated or unsaturated heterocyclic ring optionally containing 1-2 further heteroatoms selected from the group consisting of oxygen, nitrogen and sulfur.

9. The dinucleoside boranophosphate derivative of claim 6, wherein X and X' are a purine residue, wherein $R_1$ is H, $R_2$ is absent, and $R_3$ is $NH_2$; Y and Y' are OH; $Z_1$ and $Z_5$ are $O^-$; $Z_3$ is $BH_3^-$; $W_2$ and $W_3$ are O; n and n' are 0; m is 3; herein identified as compound 1 or $Ap_3$(β-B)A.

10. The dinucleoside boranophosphate derivative of claim 6, wherein X and X' are a purine residue, wherein $R_1$ is H, $R_2$ is absent, and $R_3$ is $NH_2$; Y and Y' are OH; $Z_1$, $Z_2$, $Z_4$ and $Z_5$ are $O^-$; $Z_3$ is $BH_3^-$; $W_1$, $W_2$ $W_3$ and $W_4$ are O; n and n' are 1; m is 5; herein identified as compound 3 or $Ap_5$(γ-B)A.

11. The dinucleoside boranophosphate derivative of claim 1, wherein X and X' are a pyrimidine residue, wherein $R_7$, $R_8$ and $R_{10}$ are H, and $R_9$ is O; Y and Y' are OH; $Z_1$, $Z_2$, $Z_4$ and $Z_5$ are $O^-$; $Z_3$ is $BH_3^-$; $W_1$, $W_2$, $W_3$ and $W_4$ are O; and either n and n' are 0 and m is 3, or n and n' are 1 and m is 5.

12. The dinucleoside boranophosphate derivative of claim 1, wherein X and X' are a pyrimidine residue, wherein $R_7$ and $R_8$ each independently is H, halogen, O-hydrocarbyl or S-hydrocarbyl.

13. The dinucleoside boranophosphate derivative of claim 1, wherein X and X' are a pyrimidine residue, wherein $R_7$ and $R_8$ each independently is H or $NR_{11}R_{12}$, and $R_{11}$ and $R_{12}$ each independently is H or hydrocarbyl or $R_{11}$ and $R_{12}$ together with the nitrogen atom to which they are attached form a saturated or unsaturated heterocyclic ring optionally containing 1-2 further heteroatoms selected from the group consisting of oxygen, nitrogen and sulfur.

14. The dinucleoside boranophosphate derivative of claim 11, wherein X and X' are a pyrimidine residue, wherein $R_7$, $R_8$ and $R_{10}$ are H, and $R_9$ is O; Y and Y' are OH; $Z_1$ and $Z_5$ are $O^-$; $Z_3$ is $BH_3^-$; $W_2$ and $W_3$ are O; n and n' are 0; m is 3; herein identified as compound 2 or $Up_3$(β-B)U.

15. The dinucleoside boranophosphate derivative of claim 11, wherein X and X' are a pyrimidine residue, wherein $R_7$, $R_8$ and $R_{10}$ are H, and $R_9$ is O; Y and Y' are OH; $Z_1$ and $Z_5$ are $O^-$; $Z_3$ is $BH_3^-$; $W_2$ and $W_3$ are O; n and n' are 0; m is 3; and $M^+$ is $Na^+$, namely diuridine tri(borano)phosphate tri-sodium salt.

16. The dinucleoside boranophosphate derivative of claim 11, wherein X and X' are a pyrimidine residue, wherein $R_7$, $R_8$ and $R_{10}$ are H, and $R_9$ is O; Y and Y' are OH; $Z_1$, $Z_2$, $Z_4$ and $Z_5$ are $O^-$; $Z_3$ is $BH_3^-$; $W_1$, $W_2$ $W_3$ and $W_4$ are O; n and n' are 1; m is 5; herein identified as compound 4 or $Up_5$(γ-B)U.

17. A pharmaceutical composition comprising a pharmaceutically acceptable carrier and at least one dinucleoside boranophosphate derivative of the general formula I in claim 1.

* * * * *